(12) United States Patent
Eirich et al.

(10) Patent No.: US 7,405,063 B2
(45) Date of Patent: Jul. 29, 2008

(54) **BIOOXIDATION CAPABILITIES OF *CANDIDA* SP**

(75) Inventors: L. Dudley Eirich, Milford, OH (US); Kevin W. Anderson, Indian Springs, OH (US); Jeffrey A. Gates, West Chester, OH (US); C. Ron Wilson, Loveland, OH (US); Manfred Biermann, Cincinnati, OH (US); Gilbert H. Vice, Cincinnati, OH (US)

(73) Assignee: Cognis Corporation, Cincinnati, OH (US)

( * ) Notice: Subject to any disclaimer, the term of this patent is extended or adjusted under 35 U.S.C. 154(b) by 117 days.

(21) Appl. No.: 11/035,835

(22) Filed: Jan. 14, 2005

(65) Prior Publication Data

US 2005/0181491 A1 Aug. 18, 2005

Related U.S. Application Data

(62) Division of application No. 09/812,308, filed on Mar. 20, 2001, now abandoned.

(60) Provisional application No. 60/190,626, filed on Mar. 20, 2000.

(51) Int. Cl.
*C12P 17/02* (2006.01)
*C12P 7/04* (2006.01)
*C12P 7/18* (2006.01)
*C12P 7/62* (2006.01)
*C12P 7/64* (2006.01)

(52) U.S. Cl. .................. 435/123; 435/134; 435/135; 435/146; 435/157; 435/158; 435/254.22; 435/255.4

(58) Field of Classification Search .................. 435/123, 435/134, 135, 146, 157, 158, 254.22, 255.4
See application file for complete search history.

(56) References Cited

U.S. PATENT DOCUMENTS

| | | |
|---|---|---|
| 3,057,784 A | 9/1962 | Davis et al. |
| 3,183,169 A | 5/1965 | Brillaud |
| 3,419,469 A | 12/1968 | Humphrey et al. |
| 5,254,466 A | 10/1993 | Picataggio et al. |
| 5,470,741 A | 11/1995 | Oester et al. |
| 5,620,878 A | 4/1997 | Picataggio et al. |
| 5,648,247 A | 7/1997 | Picataggio et al. |
| 5,962,285 A | 10/1999 | Anderson et al. |
| 6,004,784 A | 12/1999 | Mobley et al. |
| 6,066,480 A | 5/2000 | Mobley et al. |
| 6,288,275 B1 | 9/2001 | Turner |

FOREIGN PATENT DOCUMENTS

| | | |
|---|---|---|
| DE | 40 15 851 C1 | 8/1991 |
| DE | 40 19 166 A1 | 12/1991 |
| WO | WO 00 20566 | 4/2000 |

OTHER PUBLICATIONS

Vamecq et al., "Interactions between the ω- and β-Oxidations of Fatty Acids", *J. Biochem.* vol. 102, pp. 225-234, (1987).
Kemp et al., "Inducible long chain alcohol oxidase from alkane-grown *Candida tropicalis*", *Appl. Microbiol. and Biotechnol*, 29:370-374 (1988).
Shiio et al., "Microbial Production of Long-chain Dicarboxylic Acids from η-Alkanes", *Agr. Biol. Chem.*, vol. 35, No. 13, pp. 2033-2042 (1971).
Gilewicz et al., "Hydroxylase regulation in *Candida tropicalis* grown on alkanes", *Can.J. Microbiol.*, vol. 25, pp. 201-206 (1979).
Wislocki et al., "Reactions Catalyzed by the Cytochrome P-450 System", *Enzymatic Basis of Detoxication*, vol. 1, Chapter 7, pp. 135-182 (1980).
Okino et al., "Production of Macrocyclic Musk Compounds via Alkanedioic Acids Produced from N-Alkanes", *Flavors and Fragrances: A World Perspective.* Proceedings of the 10th International Congress of Essential Oils, Fragrances and Flavors, Lawrence, Mookherjee and Willis (Eds.), pp. 753-760 (1988).
Uemura, N; Hakko to Kogyo 43(5), 436-441 (1985).
Bühler et al., "Aliphatic Hydrocrbons", *Biotechnology*, vol. 6a, Chapter 9, pp. 329-385 (1984).
Computer Biosis 1993:233484 Liu et al. "Diterminal oxidation of decene-1 and dodecene-1 by *Candida tropicalis*" Acta Microb. Sinica (1992) vol. 32, No. 5 p. 340-345.

*Primary Examiner*—Herbert J Lilling
(74) *Attorney, Agent, or Firm*—John F. Daniels

(57) ABSTRACT

A bioprocess for producing carboxylic acids, alcohols and aldehydes is provided by culturing *Candida* sp. in a fermentation medium containing various defined substrates.

12 Claims, No Drawings

BIOOXIDATION CAPABILITIES OF *CANDIDA* SP

CROSS REFERENCE TO RELATED APPLICATIONS

This is a divisional application of U.S. patent application Ser. No. 09/812,308 filed on Mar. 20, 2001 now abandoned, which claims the benefit of U.S. Provisional Application No. 60/190,626, filed Mar. 20, 2000, the contents of which are incorporated herein by reference.

This application claims the benefit under 35 U.S.C. §119(e) of earlier filed and now abandoned U.S. Provisional Application No. 60/190,626, filed Mar. 20, 2000, the contents of which are incorporated herein by reference.

STATEMENT REGARDTNG FEDERALLY SPONSORED RESEARCH OR DEVELOPMENT

This invention was made with the United States Government support under Cooperative Agreement #70NANB8H4033 awarded by NIST. The United States Government has certain rights in the invention.

BACKGROUND

1. Technical Field

The present invention relates to the use of yeast strains to modify substrates via biooxidation. More particularly, the present invention relates to processes for converting certain substrates into alcohols or carboxylic acids utilizing yeast.

2. Background of Related Art

Aliphatic dioic acids, alcohols and compounds having combinations of alcohols and acids are versatile chemical intermediates useful as raw materials for the preparation of adhesives, fragrances, polyamides, polyesters, and antimicrobials. While chemical routes for the synthesis of long-chain $\alpha,\omega$-dicarboxylic acids are available, the synthesis is complicated and results in mixtures containing dicarboxylic acids of shorter chain lengths. As a result, extensive purification steps are necessary. While it is known that long-chain dioic acids can also be produced by microbial transformation of alkanes, fatty acids or esters, chemical synthesis has remained the preferred route, presumably due to limitations with the previously available biological approaches.

Several strains of yeast are known to excrete $\alpha,\omega$-dicarboxylic acids as a byproduct when cultured on alkanes or fatty acids. In particular, yeast belonging to the genus *Candida*, such as *C. albicans, C. cloacae, C. guillermondii, C. intermedia, C. lipolytica, C. maltosa, C. parapsilosis*, and *C. zeylenoides* are known to produce such dicarboxylic acids. (Agr. Biol. Chem. 35, 2033-2042 (1971).) In addition, various strains of the yeast *C. tropicalis* are known to produce dicarboxylic acids ranging in chain lengths from $C_{11}$ through $C_{18}$ as a byproduct when cultured on alkanes or fatty acids as the carbon source (Okino et al., B M Lawrence, B D Mookherjee and B J Willis (eds.), in *Flavors and Fragrances: A World Perspective*. Proceedings of the 10th International Conference of Essential Oils, Flavors and Fragrances, Elsevier Science Publishers BV Amsterdam (1988)), and are the basis of several patents as reviewed by Bühler and Schindler, in *Aliphatic Hydrocarbons in Biotechnology*, H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: $\alpha$-oxidation of alkanes to alcohols; $\omega$-oxidation of fatty acids to $\alpha,\omega$-dicarboxylic acids; and the degradative $\beta$-oxidation of fatty acids to $CO_2$ and water. In *C. tropicalis* the first step in the $\omega$-oxidation pathway is catalyzed by a membrane-bound enzyme complex ($\omega$-hydroxylase complex) including a cytochrome P450 monooxygenase and a NADPH-cytochrome reductase. This hydroxylase complex is responsible for the primary oxidation of the terminal methyl group in alkanes and fatty acids (Gilewicz et al., *Can. J. Microbiol.* 25:201 (1979)). The genes which encode the cytochrome P450 and NADPH reductase components of the complex have previously been identified as P450ALK and P450RED respectively, and have also been cloned and sequenced (Sanglard et al., *Gene* 76:121-136 (1989)). P450ALK has also been designated P450ALK1. More recently, ALK genes have been designated by the symbol CYP and RED genes have been designated by the symbol CPR. See, e.g., Nelson, *Pharmacogenetics* 6(1):1-42 (1996), which is incorporated herein by reference. See also Ohkuma et al., *DNA and Cell Biology* 14:163-173 (1995), Seghezzi et al., *DNA and Cell Biology*, 11:767-780 (1992) and Kargel et al., *Yeast* 12:333-348 (1996), each incorporated herein by reference. For example, P450ALK is also designated CYP52 according to the nomenclature of Nelson, supra.

Cytochromes P450 (P450s) are terminal monooxidases of the multicomponent enzyme system described above. They comprise a superfamily of proteins which exist widely in nature having been isolated from a variety of organisms, e.g., various mammals, fish, invertebrates, plants, mollusks, crustaceans, lower eukaryotes and bacteria (Nelson, supra). First discovered in rodent liver microsomes as a carbon-monoxide binding pigment as described, e.g., in Garfinkel, *Arch. Biochem. Biophys*. 77:493-509 (1958), which is incorporated herein by reference, P450s were later named based on their absorption at 450 nm in a reduced-CO coupled difference spectrum as described, e.g., in Omura et al., *J. Biol. Chem.* 239:2370-2378 (1964), which is incorporated herein by reference.

P450s catalyze the metabolism of a variety of endogenous and exogenous compounds (Nelson, supra). Endogenous compounds include steroids, prostanoids, eicosanoids, fat-soluble vitamins, fatty acids, mammalian alkaloids, leukotrines, biogenic amines and phytolexins (Nelson, supra). P450 metabolism involves such reactions as aliphatic hydroxylation, aromatic oxidation, alkene epoxidation, nitrogen dealkylation, oxidative deamination, oxygen dealkylation, nitrogen oxidation, oxidative desulfuration, oxidative dehalogenation, oxidative denitrification, nitro reduction, azo reduction, tertiary amine N-oxide reduction, arene oxide reduction and reductive dehalogenation. (P G Wislocki, G T Miwa and AYH Lu, Reaction Catalyzed by the Cytochrome P-450 System, *Enzymatic Basis of Detoxication*, Vol. 1, Academic Press (1980).) These reactions generally make the compound more water soluble, which is conducive for excretion, and more electrophilic. (These electrophilic products have detrimental effects if they react with DNA or other cellular constituents.) The electrophilic products can then react through conjugation with low molecular weight hydrophilic substances resulting in glucoronidation, sulfation, acetylation, amino acid conjugation or glutathione conjugation typically leading to inactivation and elimination as described, e.g., in Klaassen et al., *Toxicology*, 3rd ed, Macmillan, New York, 1986, incorporated herein by reference.

Fatty acids are ultimately formed from alkanes after two additional oxidation steps, catalyzed by alcohol oxidase (Kemp et al. *Appl. Microbiol. and Biotechnol*, 28, 370-374 (1988)) and aldehyde dehydrogenase. The, $\omega$-hydroxylase enzymes of the $\omega$-oxidation pathway are located in the endoplasmic reticulum, while the enzymes catalyzing the last two steps, the fatty alcohol oxidase and the fatty aldehyde dehydrogenase, are located in the peroxisomes. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.*, 102, 225-234 (1987)). In yeast, β-oxidation takes place solely in the peroxisomes (*Agr. Biol. Chem.*, 49, 1821-1828 (1985)).

Metabolic pathways can be manipulated in an attempt to increase or decrease the production of various products or by-products. Knowing that fatty acids possessing one or more internal double bonds or secondary alcohol functionality are capable of undergoing ω-oxidation, the ω-oxidation pathway can be manipulated to produce greater amounts of dicarboxylic acids. U.S. Pat. No. 5,254,466, the entire contents of which are incorporated herein by reference, discloses a method for producing β,ω-dicarboxylic acids in high yields by culturing *C. tropicalis* strains having disrupted chromosomal POX4A, POX4B and both POX5 genes. The POX4 and POX5 gene disruptions effectively block the β-oxidation pathway at its first reaction (which is catalyzed by acyl-CoA oxidase) in a *C. tropicalis* host strain. The POX4 and POX5 genes encode distinct subunits of long chain acyl-CoA oxidase, which are the peroxisomal polypeptides (PXPs) designated PXP-4 and PXP-5, respectively. The disruption of these genes results in a complete block of the β-oxidation pathway thus allowing enhanced yields of dicarboxylic acid by redirecting the substrate toward the ω-oxidation pathway and also preventing reutilization of the dicarboxylic acid products through the β-oxidation pathway.

Similarly, *C. tropicalis* may also have one or more cytochrome P450 genes and/or reductase genes amplified which results in an increase in the amount of rate-limiting ω-hydroxylase through P450 gene amplification and an increase in the rate of substrate flow through the ω-oxidation pathway. *C. tropicalis* strain AR40 is an amplified H 5343 strain wherein all four POX4 genes and both copies of the chromosomal POX5 genes are disrupted by a URA3 selectable marker and which also contains 3 additional copies of the cytochrome P450 gene and 2 additional copies of the reductase gene, the P450RED gene. Strain AR40 has the ATCC accession number ATCC 20987. *C. tropicalis* strain R24 is an amplified H 5343 strain in which all four POX4 genes and both copies of the chromosomal POX5 genes are disrupted by a URA3 selectable marker and which also contains multiple copies of the reductase gene. Strains AR40 and R24 are described in U.S. Pat. Nos. 5,620,878 and 5,648,247, the contents of which are incorporated herein by reference.

Processes for utilizing modified *C. tropicalis* to produce carboxylic acids are also known. U.S. Pat. No. 5,962,285, the entire contents of which are incorporated herein by reference, discloses a process for making carboxylic acids by fermenting a β-oxidation blocked *C. tropicalis* cell in a culture comprised of a nitrogen source, an organic substrate and a cosubstrate. The substrate is an unsaturated aliphatic compound having at least one internal carbon-carbon double bond and at least one terminal methyl group, a terminal carboxyl group and/or a terminal functional group which is oxidizable to a carboxyl group. The fermentation product is then reacted with an oxidizing agent to produce one or more carboxylic acids.

Similar shake flask experiments have been used in the past to test substrates. The terminal methyl group and the terminal double bond of α-alkenes or branched monoacids are oxidized and form alcohol groups or the desired acid groups. The oxidation of the terminal double bond of α-olefins to form a (ω,ω-1) diol is an interesting reaction. The overall oxidation product is thus a (ω,ω-1) hydroxyfatty acid. The biooxidation of α-olefins was first reported by Uemura. (N. Uemura, Industrialization of the Production of Dibasic Acid from n-Paraffins Using Microorganisms, Hakko to Kogyo, 43:436-44 (1985).).

While the genetically modified strains of *Candida* sp. are able to produce large quantities of product necessary to develop a commercially feasible process, it is not known what effect variations of chain length, functional groups, etc. will have on the ability of *C. tropicalis* to produce alcohols and carboxylic acids through the process of biooxidation.

SUMMARY OF THE INVENTION

In accordance with the present invention, it has been determined that in order for terminal methyl groups of organic substrates to be oxidized by *Candida* sp., at least one methylene group must be present between a terminal methyl group and the rest of the molecule. Accordingly, the inventors have developed a process by which substrates of varying functionality, chain lengths and overall structure are oxidized by *Candida* sp. to alcohols and carboxylic acids.

In one embodiment, the substrate is solubilized in an organic solvent and then biooxidized by *Candida* sp.

In a preferred embodiment, the *Candida* sp. used in the bioconversion process has been modified so that its β-oxidation pathway has been blocked. In another preferred embodiment, the *Candida* sp. used in the bioconversion process has been modified so that its β-oxidation pathway has been blocked and one or more of its cytochrome P450 genes and/or reductase genes have been amplified.

DESCRIPTION OF THE PREFERRED EMBODIMENTS

For purposes of the present invention, a carboxylic acid includes a polycarboxylic acid. Toxicity is the highest concentration at which a substrate can be added to a culture broth of *Candida* sp. without causing undue inhibition of growth, unacceptable amounts of cell death or undue interference with the bioconversion process.

This invention provides a process for introducing hydroxyl, aldehyde and/or carboxylic acid functionalities into organic substrates by fermentation with by *Candida* sp. Examples of suitable particular *Candida* sp. useful herein include *C. albicans*, *C. cloacae*, *C. guillermondii*, *C. intermedia*, *C. lipolytica*, *C. maltosa*, *C. parapsilosis*, and *C. zeylenoides* and *C. tropicalis*. While it is known that certain alkane and fatty acid substrates with terminal methyl groups can be oxidized to form alcohols or carboxylic acids and that fatty acids possessing one or more internal double bonds or secondary alcohol functionality are capable of undergoing ω-oxidation, the effects of additional functionality, such as double bonds, alcohol groups, etc. were unknown in the biooxidation process. According to the present invention, it has been determined that the overall capability of *Candida* sp. to perform biochemical oxidations on a variety of chemical substrates is dependent on the presence of at least one methylene group between a terminal methyl group and the rest of a substrate molecule. In the first phase of this testing, substrates were selected because they contained a terminal methyl group. In addition, they possessed additional functionality such as a double bond, alcohol group, etc. Classes of substrates tested included primary and secondary alcohols, α-olefins, ketones, epoxides, alkenes, alkynes, sulfur compounds, branched-chain fatty acids, Guerbet alcohols, fatty acid esters, natural oils, and sterols. A second phase of testing was conducted on additional substrates, including a homologous series of varying aliphatic chain lengths attached to a cyclohexane ring. The second series of tests obtained additional information about the oxidation products using analysis by gas chromatography-mass spectrometry (GC/MS) in addition to IR and NMR analyses.

A preferred species of *Candida* sp. is *C. tropicalis*. Although wild-type *C. tropicalis* may be utilized to convert substrates, according to the present invention strains in which the β-oxidation pathway is partially blocked, are preferred. For example, genetically modified *C. tropicalis* having chromosomal POX4A, POX4B and POX5 genes disrupted to block β-oxidation pathway may be utilized. Examples of strains of *C. tropicalis* which are partially β-oxidation blocked include, H41, H41B, H51, H45, H43, H53, H534, H534B and H435 as described in aforementioned U.S. Pat. No. 5,254,466. An example of a completely β-oxidation blocked strain of *C. tropicalis* wherein all POX4 and POX5 genes are disrupted is H5343 (ATCC 20962) as described in U.S. Pat. No. 5,254,466. The sequence in which the four POX genes are disrupted is immaterial. When all of these POX genes are disrupted, they no longer encode the functional acyl-CoA oxidase isozymes necessary for the β-oxidation pathway. Therefore, the substrate flow in this strain is redirected to the ω-oxidation pathway as the result of functional inactivation of the competing β-oxidation pathway by POX gene disruption. In another preferred embodiment, *C. tropicalis* strains having one or more cytochrome P450 genes and/or reductase genes amplified may be utilized. For example, *C. tropicalis* strains which have a greater number of CPR genes than the wild type strain have shown increased productivity of carboxylic acids as described, e.g., in aforementioned U.S. Pat. No. 5,620,878. Specific examples of CPR genes include the CPRA and CPRB genes of *C. tropicalis* 20336 as described, e.g., in U.S. application Ser. No. 09/302/620 and International Application No. PCT/US99/2097, each incorporated herein by reference. These strains provide an increase in the amount of rate-limiting ω-hydroxylase and an increase in the rate of substrate flow through the ω-oxidation pathway. Preferred strains of *C. tropicalis* are H5343 (ATCC Accession No. 20962), AR40 (ATCC No. 20987) and R24. See U.S. Pat. Nos. 5,620,878 and 5,648,247.

The genetically β-oxidation blocked strain of *C. tropicalis* used in a preferred embodiment has been shown previously to perform a ω-oxidation reaction on the terminal methyl group of long-chain fatty acids and alkanes. While the preferred strain of *C. tropicalis* is a β-oxidation-blocked strain, any *C. tropicalis* strain, no matter whether the strain can perform β-oxidation or not, may be used. A complete or partial block in β-oxidation only decreases the probability that the substrates tested or their oxidation products will be degraded, and increases the likelihood of detecting biooxidation products, if formed. With some substrates, there is also the possibility that degradation might occur through pathways other than β-oxidation. Therefore, some observed loss of starting material might be due to degradation rather than volatility, although volatility of substrates is the most likely cause for low recoveries.

In one embodiment of the invention, the substrate to be converted is solubilized in a solvent. In a preferred embodiment, the solvent is an organic solvent such as acetone, ethanol, or hexane, with acetone being most preferred. The solvent is utilized in amounts that are not toxic to *Candida* sp. but still capable of solubilizing the substrate.

Substrates themselves should be tested for their toxicity prior to bioconversion. The data obtained from these experiment is useful in three ways: 1) it ensures that *Candida* sp. remain viable after induction and can adequately perform the biooxidation process; 2) the volatility of test substrates can be assessed; and 3) knowing the toxicity of a test substrate ensures that the maximum amount of sample can be added.

The organic substrate is any organic compound having at least one terminal methyl group attached to at least one methylene group. Examples of organic substrates which can be used in the process according to the invention include but are not limited to $CH_3CH_2$-ethers, $CH_3CH_2$-epoxides, $CH_3CH_2$-saturated primary alcohols, $CH_3CH_2$-alkoxy, $CH_3CH_2$-diols and $CH_3$—$CH_2$ diol esters. In addition to the above, the organic substrate which can be used in the process according to the invention include but are not limited to $CH_3CH_2$-cycloalkyl, $CH_3$, $CH_2$-aryl and the like.

The fermentation step is preferably carried out in two stages. In the first stage, a culture medium is inoculated with an active culture of *Candida* sp. such as β-oxidation blocked *C. tropicalis* strain where a period of rapid exponential growth occurs. In the second stage, which occurs as the cell growth of the first stage enters stationary phase, the substrate is added wherein the biooxidation described herein takes place. Since energy can no longer be produced from the substrate in β-oxidation blocked strains, it is necessary to add a cosubstrate. The cosubstrate is a fermentable carbohydrate such as glucose, fructose, maltose, glycerol and sodium acetate. For larger industrial fermentations, the preferred cosubstrate is glucose, preferably a liquid glucose syrup, for example, 95% dextrose-equivalent syrup, or even lower dextrose-equivalent syrups. For shake flask experiments, the preferred cosubstrate is glycerol. Such materials contain small amounts of disaccharides, trisaccharides, and polysaccharides which can be hydrolyzed during the fermentation by the addition of an amylase enzyme such as α-amylase, glucoamylase and cellulase. Thus glucose can be provided in situ in a reaction simultaneous with the biooxidation. The fermentation conditions and procedures are similar to those disclosed in U.S. Pat. No. 5,254,466.

The fermentation step can be modified by utilizing a triglyceride fat or oil as the source of both the organic substrate and cosubstrate. A lipase, formulated with the fermentation broth, hydrolyzes or splits the fat or oil into fatty acids and glycerine. Glycerine consumption by the organism serves to drive the splitting reaction to completion while supplying the energy necessary to convert the free fatty acids to their corresponding alcohols or acids. Lipases that are oleo-specific are particularly preferred. Oleo-specific lipases exhibit a high selectivity for a triglyceride having a high oleic acid content and selectively catalyze the hydrolysis of the oleate ester groups. Examples of such oleo-specific lipases include but are not limited to the lipases produced by *Pseudomonas* sp, *Humicola lanuginosa, Candida rugosa, Geotrichum candidum*, and *Pseudomonas (Burkholderia)*. A particularly preferred lipase is UNLipase from *Geotrichum candidum* ATCC No. 74170 described in U.S. Pat. No. 5,470,741, the entire contents of which are incorporated herein by reference.

After the substrates were added to *Candida* sp. and biooxidation occurred, samples were obtained, dried and analyzed. Those skilled in the art are familiar with many techniques for purification and analysis of alcohols, aldehydes and carboxylic acids. In the present case, the dried samples were weighed and dissolved in an NMR appropriate solvent. $C_{13}$ and H-NMR were performed on an adequate amount of recovered sample using a Varian Unity 400 (Varian, Inc.).

However, analysis via NMR-spectroscopy has its limitations. It can only estimate what changes occurred and identify functional groups, but not identify the actual compounds that have been synthesized. In complex mixtures, particularly, NMR may miss a small amount of oxidation product altogether. Additionally the extraction process solubilized a number of cellular components, such as cell membrane lipids and other fatty acids produced from the added carbon source (glycerol). Antifoam was also detected. Therefore, for complex mixtures with only small amounts of product formation, it might be useful to use IR, GC/MS, LC/MS, HPLC/MS or other analytical techniques for a more accurate and precise analysis. IR can be performed using, for example, a Nicolet Magna-IR 560.

In a preferred embodiment, GC/MS is also performed. Samples are silylated prior to GC/MS analysis, but acetylation and methylation may also be performed with certain samples, to make derivatives. Derivatives aid in interpretation of the mass spectra by making the compound better suited for structure elucidation, particularly for identification of hydroxy derivatives by silylation. These molecular weight differences assist in assigning structures to components of samples. Samples may be separated using any procedure known to those skilled in the art, such as a J&W DB-5MS (60 m×0.25 mm×0.25 um) column (J&W Scientific, Folsom, Calif.). GC/MS can be performed on any suitable apparatus that permits accurate readings following the manufacturer's protocol, such as an AutoSpec X015 VG (Micromass Ltd., Manchester, England) triple sector mass spectrometer (E-B-E configuration).

The results indicate that *Candida* sp. possess significant genetic and biochemical variability, since they have the capability to oxidize methyl groups attached to a variety of R-groups. Tests with a homologous series of aliphatic chains attached to cyclohexane (methylcyclohexane, ethylcyclohexane, propylcyclohexane, and butylcyclohexane) indicate that the methyl group must be part of an aliphatic chain of at least two carbons (ethyl group). To date, no evidence of oxidation of a secondary, tertiary, or aromatic methyl group has been observed. Most substrates tested herein have the general formula: R—$(CH_2)_n$—$CH_3$, where R is an epoxide, alkoxy, ether, saturated primary alcohol, cycloalkyl, aryl, diol, or diol ester. Substrates were selected that allowed the determination of the minimum chain length required for oxidation (n in the formula). Other substrates were selected to determine what types of functional groups (R in the formula) are compatible with biooxidation.

The results of the experiments clearly indicate that the terminal methyl groups of propyl and butyl chains (or larger) attached to a variety of functional groups can be oxidized by *Candida* sp. Overall, oxidation was seen where a terminal methyl group was adjacent to a methylene group. Accordingly, depending upon the number of such groups, monoacids, diacids, triacids, etc. could be produced. Likewise, the number of OH groups and CHO groups generated by biooxidation will vary based on the number of suitable terminal methyl groups. Oxidation of substrates having branched structures which provides multiple terminal methyl groups will produce greater numbers of oxidized species. In addition, the results with ethylcyclohexane indicate that the terminal methyl group of the ethyl chain can also be oxidized. The successful oxidation given the bulkiness of the cyclohexyl moiety would indicate that ethyl groups attached to other functionalities are oxidizable at the terminal methyl group as well. The evidence available indicates that n in the previously described formula is 1 or higher.

The results indicate that an aliphatic chain can be attached to a variety of functional groups without preventing biooxidation of the terminal methyl group as long as a methylene separates the terminal methyl group from the rest of the molecule. If substrates and/or products contain both an acid and alcohol functionality, esterification between acid and alcohol groups is observed to occur to a certain extent. Without wishing to be bound by any theory, this is likely catalyzed by either internal or external lipases, which are known to catalyze esterification reactions in hydrophobic environments. Epoxy groups are opened to form diols. All epoxy groups of the Soybean oil Plastolein 9232 (epoxy soya) were opened. This observation has now been confirmed by finding that 1,2-epoxytetradecane is oxidized to yield the corresponding ($\omega,\omega$-1)-hydroxyfatty acid. Primary aliphatic alcohols are oxidized at the terminal methyl to yield alcohols or diacids. Shorter chain alcohols, such as dodecanol, show an unusually low degree of reaction that may be due to the inhibition of growth due to lauric acid product formation. The series butylcyclohexane, propylcyclohexane, ethylcyclohexane, and methylcyclohexane, was tested to determine the minimal aliphatic chain length needed for oxidation of the terminal methyl group to occur. The results described below indicate that the minimal chain length is two (ethyl group). No oxidation of aliphatic chain lengths shorter than two (methyl group) has been observed.

In order to achieve a higher yield of oxidation product or to allow the oxidation to go to completion (—$CH_3$→—$CH_2OH$→—$CHO$→—$COOH$), the process of biooxidation could be prolonged to 72 hours or more. One method for doing this would be to add another batch of carbon source and/or sample after the initial time period. Very volatile samples should be added more often during the biooxidation process as well as samples that can only be added at lower concentrations (to avoid toxicity).

The following examples are merely illustrative of certain aspects of the invention and should not be construed as limiting the invention in any manner.

EXAMPLE 1

Toxicity Tests of Organic Solvents

Since some of the substrates were solid at room temperature or were added at low concentrations, they were first solubilized in an organic solvent, prior to their addition to the yeast culture. Since some solvents exhibit toxicity to *Candida* sp., one of the first steps was to evaluate the toxicity of four potential organic solvents: acetone, chloroform, ethanol and hexane. These solvents were chosen because of their potential for solubilizing the majority of the test substrates. Acetone in particular was considered to be a good solvent, since it could solubilize most of the organic substrates to be tested, yet was itself soluble in the aqueous culture medium. The concentration at which a test solvent became lethal to *Candida* sp. was determined by testing its ability to grow in the presence of different solvents at different concentrations. Cell growth in the presence of the different solvents was monitored spectrophotometrically using a Shimadzu UV160A UV-visible recording spectrophotometer.

For each solvent tested, YPD was added to five autoclaved glass tubes. 6 ml was transferred to the first and 3 ml to the rest. 4% solvent was added to the first tube. Then the solvents were serially diluted to give concentrations from 4% to 0.25% by pipetting 3 ml from one tube to another. The tubes were mixed well between transfers. To achieve the serial dilution for chloroform and hexane, which are not soluble in aqueous solutions, it was necessary to pipette up and down or vortex until a uniform suspension formed. After completing the dilutions, 10 ml of an overnight grown YPD culture of *C. tropicalis* was added to each tube and the culture was allowed to grow in the presence of the solvents. As a positive control, one culture was inoculated in YPD alone. After 24 h in a 30° C. shaker at 220 rpm the cultures were sampled. The samples were then diluted in YPD 1:100 and the absorbance (ABS) measured spectrophotometrically at a wavelength of 600 nm as an indicator for growth. Each culture was also examined under the microscope.

The results of this test are shown below in Table 1. Three out of four solvents were found to be useful. In addition to being a very good solvent, acetone was found to be nontoxic at concentrations of 4% or lower. Because of this, it was the solvent of choice for the majority of the substrates. Both ethanol, which was found to be nontoxic at 4%, and hexane, which was found to be nontoxic at 2%, were found to be suitable solvents. Chloroform was not an acceptable solvent, since it was found to be lethal at concentrations greater than 1% and it precipitated various components of the broth at these concentrations. Growth of *C. tropicalis* strain H5343 was measured by absorbance at 600 nm.

TABLE 1

Spectrophotometric Data of Toxicity tests of Organic Solvents

ABS Lambda = 600.0 nm
Dilution in YPD (1:100)
Concentration [%]

| Organic Solvent | 4 | 2 | 1 | 0.5 | 0.25 |
|---|---|---|---|---|---|
| Acetone | 0.087 | 0.149 | 0.111 | 0.183 | 0.123 |
| Chloroform | 0.000 | 0.000 | 0.005 | 0.168 | 0.156 |
| Ethanol | 0.090 | 0.119 | 0.137 | 0.104 | 0.122 |
| Hexane | 0.005 | 0.126 | 0.119 | 0.148 | 0.119 |

EXAMPLE 2

Toxicity Tests of Substrates

This experiment examined the toxicity of test substrates. The data collected from Example 1 was used to help prepare a stock solution of the test substrate in one of the solvents. Stock solutions of most substrates in concentrations from 100 g/L to 500 g/L were made using acetone as a solvent. Aqueous solutions of polyethylene glycol were prepared. In the few cases that the substrate could not be dissolved in any of the tested solvents, it was added neat.

The toxicity test used here was similar to that used for the solvents described in Example 1. The goal was to determine the highest concentration at which a substrate could be added to a culture broth without being toxic, inhibiting growth, or interfering with the bioconversion process. *C. tropicalis* strain H5343 was grown in the presence of the substrate at different concentrations and growth was monitored spectrophotometrically. In order to determine if the substrate was lethal or was simply inhibiting growth, the cultures were examined under the microscope and streak plates of YPD and LB agar were prepared. Contamination of the culture with an unwanted organism could also be detected using this approach. Table 2 lists the substrates that were tested along with their source.

TABLE 2

| Substrates Tested | | | |
|---|---|---|---|
| Substrate | Vendor | CAS No. | Purity [%] |
| 1-Dodecanol | n/a | 112-53-8 | n/a |
| 2-Ethylhexanoic acid | Henkel | 149-57-5 | n/a |
| 2-Heptylundecanoic acid | Henkel | n/a | n/a |
| 6-Dodecyne | Lancaster | 6975-99-1 | n/a |
| 6-Undecanol | Fluka | n/a | n/a |
| 9-Heptadecanone | n/a | n/a | n/a |
| 12-Hydroxystearic acid | Lancaster | 106-14-9 | 96 |
| $C_{12}$ α-Olefin | Shell | 112-41-4 | n/a |
| $C_{14}$ α-Olefin | Shell | 1120-36-1 | n/a |
| Castor Oil | n/a | 8001-79-4 | n/a |
| Dodecyclamine | Aldrich | 124-22-1 | 98 |
| E 993 Aliphat 34R | Henkel | n/a | n/a |
| Emery 9232, Pastolein | Henkel | n/a | n/a |
| Eutanol G16 | Henkel | n/a | n/a |
| Generol | Henkel | n/a | n/a |
| HD-Ocenol | Henkel | n/a | n/a |
| Hexadecyl acetate | Henkel | 3551-84-01 | n/a |
| Hexadecyl pelargonate | Henkel | 3551-86 | n/a |
| Indu-Extrakt-sclareol | Henkel | n/a | n/a |
| Larol alcohol C12-14A | Henkel | n/a | n/a |
| PEG 200 | Lancaster | 25322-68-3 | n/a |
| PEG 200, Dilaurate | Henkel | n/a | n/a |
| PEG 200, Monolaurate | Henkel | n/a | n/a |
| R(+) limonene | Aldrich | 5989-27-5 | 97 |
| S(−) limonene | Aldrich | 5989-54-8 | 96 |
| trans-2-nonene | Aldrich | 6434-78-2 | 99 |
| trans-2-tetradecene | Aldrich | 41446-63-3 | 98 |

For each substrate tested, YPD was added to five autoclaved glass tubes. 6 ml was transferred to the first tube and 3 ml to the rest. 1% substrate was added to the first tube and then serially diluted to give concentrations from 1% to 0.015%. Since the last tube was initially empty, the concentration in the last two tubes was the same. Except for the last tube, 10 ml of an overnight YPD culture of *C. tropicalis* was added to each tube, the last tube was a control for contamination. The cultures were then allowed to grow in the presence of the substrates. As a growth-control one culture without substrate was inoculated. After 48 h in a 30° C. shaker at 220 rpm the cultures were sampled. The samples were then diluted in YPD 1:100 and growth was measured spectrophotometrically at a wavelength of 600 nm.

To determine if contamination had occurred, each culture was examined under the microscope and streak plates of both YPD and LB were made from the 1% and the inoculated 0.015% tube.

Table 3 below shows that most substrates were not toxic at a concentration of 1% or less. Some, however, were found to be highly toxic to *C. tropicalis* and were not suitable for further testing.

TABLE 3

Spectrophotometric Data of Toxicity tests of Substrates

ABS 1 = 600.0 nm
Dilution in YPD (1:100)

| Substrate | Concentration [%] | | | | | | | neg. control |
|---|---|---|---|---|---|---|---|---|
| | 1 | 0.5 | 0.25 | 0.13 | 0.063 | 0.0313 | 0.01563 | |
| 1-Dodecanol | 0.267** | 0.013** | 0.032** | 0.004 | 0.000 | 0.000 | 0.000 | 0.000 |
| 2-Ethylhexanoic acid | 0.000 | 0.000 | 0.000 | 0.000 | 0.000 | 0.051 | 0.099 | 0.000 |
| 2-Heptylundecanoic acid | 0.268 | 0.048 | — | 0.043 | 0.077 | 0.077 | 0.082 | 0.000 |
| 6-Dodecyne | 0.066 | 0.071 | 0.073 | 0.071 | 0.074 | 0.083 | 0.125 | 0.000 |
| 6-Undecanol | 0.000** | 0.000** | 0.000** | 0.000** | 0.000** | 0.000** | 0.000** | 0.000 |

TABLE 3-continued

Spectrophotometric Data of Toxicity tests of Substrates

ABS 1 = 600.0 nm
Dilution in YPD (1:100)

| Substrate | Concentration [%] | | | | | | | neg. control |
|---|---|---|---|---|---|---|---|---|
| | 1 | 0.5 | 0.25 | 0.13 | 0.063 | 0.0313 | 0.01563 | |
| 9-Heptadecanone | 0.004** | 0.073 | 0.120 | 0.103 | 0.064 | 0.120 | 0.100 | 0.000 |
| 12-Hydroxystearic acid | 0.120 | NT | NT | NT | NT | NT | NT | NT |
| C12 a-Olefin | 0.082 | 0.080 | 0.080 | 0.082 | 0.119 | 0.119 | 0.077 | 0.000 |
| C14 a-Olefin | 0.087 | 0.084 | 0.115 | 0.097 | 0.085 | 0.084 | 0.061 | 0.000 |
| Castor Oil | 0.078 | 0.082 | 0.089 | 0.086 | 0.070 | 0.090 | 0.077 | 0.000 |
| Dodecene | 0.026 | 0.032 | 0.053 | 0.050 | 0.079 | 0.055 | 0.088 | 0.000 |
| Dodecyclamine | 0.000 | 0.000 | 0.000 | 0.000 | 0.000 | 0.000 | 0.000 | 0.000 |
| E 993 Aliphat 34R | 0.093 | 0.098 | 0.091 | 0.102 | 0.093 | 0.081 | 0.112 | 0.000 |
| Emery 9232, Pastolein | 0.061 | NT | 0.076 | 0.107 | 0.870 | 0.055 | 0.059 | 0.000 |
| Eutanol G16 | 0.117 | 0.122 | 0.145 | 0.273 | 0.110 | 0.145 | 0.120 | 0.000 |
| Generol | 0.053* | 0.044* | 0.011* | 0.122 | 0.139 | 0.145 | 0.148 | 0.000 |
| HD-Ocenol | 0.087 | 0.085 | 0.097 | 0.115 | 0.076 | 0.087 | 0.093 | 0.000 |
| Hexadecyl acetate | 0.155 | 0.103 | 0.110 | 0.083 | 0.089 | 0.104 | 0.110 | 0.000 |
| Hexadecyl pelargonate | 0.080 | 0.102 | 0.103 | 0.083 | 0.075 | 0.095 | 0.112 | 0.000 |
| Indu-Extrakt-sclareol | 0.083 | 0.092 | 0.110 | 0.106 | 0.157 | 0.100 | 0.083 | 0.000 |
| Larol alcohol C12-14A | NT | NT | NT | NT | NT | NT | NT | NT |
| PEG 200 | 0.089 | 0.096 | 0.101 | 0.096 | 0.103 | 0.108 | 0.101 | 0.000 |
| PEG 200, Dilaurate | 0.051** | 0.064 | 0.088 | 0.061 | 0.057 | 0.080 | 0.064 | 0.000 |
| PEG 200, Monolaurate | 0.041** | 0.052 | 0.099 | 0.107 | 0.090 | 0.107 | 0.062 | 0.000 |
| R(+) limonene | 0.000 | 0.000 | 0.000 | 0.007 | 0.106 | 0.117 | 0.123 | 0.000 |
| S(−) limonene | 0.002 | 0.002 | 0.000 | 0.002 | 0.011 | 0.094 | 0.104 | 0.000 |
| trans-2-nonene | 0.000 | 0.000 | 0.000 | 0.066 | 0.105 | 0.100 | 0.112 | 0.000 |
| trans-7-tetradecene | 0.095 | 0.107 | 0.103 | 0.104 | 0.112 | 0.106 | 0.117 | 0.000 |

ABS = absorbance of culture broth
NT => not tested
**growth inhibited, cells still alive as detected on streak plates. Abs result of substrate interference
*no growth detected on streak plates, therefore, possible substrate interference

EXAMPLE 3

Bioconversion Process (Phase 1)

The maximum non-toxic concentration of each substrate, as determined from the toxicity testing in Example 2, was employed for the bioconversion testing in shake flask experiments. Since the majority of substrates tested were not toxic at 1%, the experiments were carried out in a volume of 50 ml in a 500 ml baffled shake flask. The test substrate was added as a stock solution dissolved or diluted in an appropriate solvent (generally acetone). Polyethylene glycol and its derivatives, however, were dissolved either in water or were added neat, depending on viscosity and solubility. Each experiment was done in duplicate. A control without the organism was run for each substrate to verify that chemical modifications were the result of the bioconversion by *Candida*. The uninoculated controls were run under the same conditions as the inoculated flasks.

The bioconversion tests were undertaken following a shake flask protocol. On the first day, 100 ml of YPD was inoculated with a fresh colony of *C. tropicalis* H5343 in a 1000 ml baffled shake flask. The YPD contained 3 g/L BACTO® Yeast extract (Difco), 20 g/L BACTO® Peptone (Difco), and 20 g/L BACTO® Dextrose (Difco). One drop of SAG471 (commercially available from Witco) concentrate was added as an antifoaming agent. The culture was then incubated in a 30° C. shaker at 300 rpm for 20 hours.

After a growth phase of 20 hours, the 100 ml YPD culture was transferred to 900 ml YM-Broth. The YM-Broth contained 3 g/L BACTO® Yeast Extract, 3 g/L BACTO® Malt Extract, 5 g/L BACTO® Peptone, and 10 g/L BACTO® Dextrose. The 1000 ml was dispensed to five 2000 ml baffled shake flasks in 200 ml aliquots. Again, one drop of SAG471 concentrate was added to each flask. The cultures were then allowed to grow for 30 hours in a 30° C. shaker at 300 rpm.

The cells were then centrifuged for 5 min. at 4068 g at room temperature. The supernatant was discarded and the cells were resuspended in 1000 ml DCA3. DCA3 is a 0.3 M potassium phosphate buffer, pH 7.5, containing 50 g/L glycerol and 6.7 g/L yeast nitrogen base. After resuspension, 50 ml was transferred to 500 ml baffled shake flasks. The substrate was then added at the optimal concentration determined in the toxicity test described above in Example 2. One drop of SAG 471 concentrate was added to each flask prior to incubation for 48 hours in a 30° C. shaker at 300 rpm.

After 48 hours, the cultures were transferred to 50 ml Falcon tubes and stored frozen at −20° C. until analyzed.

In the standard procedure for extraction, the whole sample was poured into a separation funnel and acidified with 5 ml HCl [12N]. A mix of 30 ml diethyl ether and 20 ml petroleum ether was added and the separation funnel was extracted using standard extraction protocols. The water phase was removed to another separation funnel. Again, a mix of 30 ml diethyl ether and 20 ml petroleum ether was added and the separation funnel shaken in the usual manner. The water phase was then discarded. Water was added to both separation funnels, which were shaken again. The water phase was discarded and both ether phases were combined and filtered into preweighed beakers through sodium sulfate to remove any remaining water. The solvent was then allowed to evaporate in the hood to leave the dried sample behind.

Due to its water-solubility, polyethylene glycol and its derivatives. required a different extraction method. 10 ml of sample broth was diluted with 90 ml HPLC-grade acetone and anhydrous magnesium sulfate was added to remove the water. The suspension was stirred for 1-2 min and was subsequently filtered into a preweighed beaker. The filter residue was rinsed with HPLC-grade acetone and the pooled acetone fractions were allowed to evaporate in the hood. The dried sample was weighed and dissolved in an NMR appropriate solvent. $C_{13}$ and H-NMR were performed with an adequate amount of recovered sample on a Varian Unity 400 (commercially available from Varian, Inc.).

EXAMPLE 4

Bioconversion of Dodecene

The bioconversion of dodecene was tested following the procedures set forth in Example 3. A low amount of sample was recovered, about 10% of the starting weight, part of which was the SAG 471 antifoam. The recovered material had significantly reduced α-olefin and terminal $CH_3$. The NMR on the sample obtained showed that one major functionality is carboxylic acid. Another is 1,2-diol. It is not certain from the spectra whether there is any $C_{12}$ di-acid or if the product is predominantly 11,12-dihydroxydodecanoic acid. Interestingly, a little fatty type unsaturation and polyunsaturation was seen. A minor amount of some unknown aromatic was also seen.

EXAMPLE 5

Bioconversion of 1-tetradecene

The bioconversion of 1-tetradecene was tested following the procedures set forth in Example 3. Recovery was 0.16 g (32%). The NMR analysis was very similar to Example 4. Again, $CH_3$ and α-olefin were reduced significantly (not necessarily on the same molecules). Again, significant acid was formed, and the 1,2-diol was more distinct, indicating 13,14-dihydroxytetradecanoic acid. Some internal unsaturation was also seen, indicating undesired microbial fatty acid modification. No triglyceride was seen, despite glycerin being utilized as a nutrient.

EXAMPLE 6

Bioconversion of 2-heptylundecanoic Acid

The bioconversion of 2-heptylundecanoic acid was tested following the procedures set forth in Example 3. Recovery was 0.38 g (76%). NMR analysis showed approximately 25% reduction of the chain terminal $CH_3$. A significant part of this reduced $CH_3$ is present as primary hydroxyl and ester of primary hydroxyl. Products formed include hydroxylated 2-heptylundecanoic acid and carboxy-2-heptylundecanoic acid. Interestingly, a small amount of unsaturation, typical of fatty unsaturation, was also seen, plus the $CH_2$ between olefin groups of fatty polyunsaturation, indicating the organism can convert some of this branched acid to oleic and linoleic acids. Samples from the control showed NMR peaks as expected for the title substrate, along with a small amount of ester of the incompletely oxidized residual alcohol.

EXAMPLE 7

Bioconversion of 1-dodecanol

The bioconversion of 1-dodecanol was tested following the procedures set forth in Example 3. Recovery was 0.22 g (44%). IR analysis showed acid, ester, and hydroxyl. NMR analysis showed little, if any reduction of the terminal $CH_3$ to dodecanedioic acid. Apparently approximately 25% of the alcohol functionality oxidized to dodecanoic acid, some of which then esterified. Also, some of the alcohol was oxidized to the n-aldehyde. Approximately 0.4% of the product was n-aldehyde, 4.5-5% was dehydrated aldol condensate, and approximately 12% was aldehyde di-alkyl acetal. Products seen include dodecanal, dodecanoic acid, and 1,12-dodecanedioic acid. In the control, only the starting 1-dodecanol was detected.

EXAMPLE 8

Bioconversion of 6-undecanol

The bioconversion of 6-undecanol was tested following the procedures set forth in Example 3. Only 0.14 g, about 28% of the starting weight, was recovered in the extract, indicating that most of the substrate was either totally consumed by the organism, lost to evaporation, or somehow lost in extraction. The extract recovered was nearly identical to the starting material, with the addition of a little SAG 471 antifoam containing polypropylene glycol.

EXAMPLE 9

Bioconversion of 12-hydroxystearic acid

The bioconversion of 12-hydroxystearic acid was tested following the procedures set forth in Example 3. The starting material is about 4% self-esterified, and contains about 4% 12-ketostearic acid. 0.39 g or 78% of sample was recovered. NMR analysis on the control showed no reaction. The finished extract showed a slight decrease of the keto group, a slight decrease in ester, and a slight increase in unsaturation, from about 1% to about 2%. Of most significance, however, is that the presence of terminal $CH_3$ dropped about 25%, apparently by oxidation to the acid, 7-hydroxyoctadecanedioic acid.

EXAMPLE 10

Bioconversion of Castor Oil

The bioconversion of castor oil was tested following the procedures set forth in Example 3. Recovery was 0.20 g (40%). NMR analysis on the products showed that the terminal $CH_3$ was about 25% gone, to 7-hydroxy-9-octadecene-1,18-dioic acid, since no primary alcohol or ester of primary alcohol was seen. However, the triglyceride functionality and the chain secondary hydroxy have undergone an apparent random transesterification, yielding a mix of mono-, di-, and triglycerides, plus an ester of secondary OH and residual free secondary OH. Also seen at a minor level was the ester of 2-enoic acid, possibly formed by oxidation at the secondary hydroxyl. A few other small NMR peaks were unidentified. NMR analysis of the control reaction showed only peaks expected for castor oil, with a little random transesterification (1,2 and 1,3-diglycerides and esterified chain secondary OH), much lower than in the bio-oxidized product. The control sample also showed none of the 2-enoate observed in the bio-oxidized product.

EXAMPLE 11

Bioconversion of Plastolein 9232 (Epoxidized Soybean Oil—Epoxy Soya)

The bioconversion of Plastolein 9232 (epoxidized soybean oil) was tested following the procedures set forth in Example 3. 0.17 g of the initial sample (34%) was recovered. NMR analysis showed terminal $CH_3$ was nearly all gone, apparently oxidized to polycarboxy polyhydroxy soybean oil. The epoxy groups were nearly completely opened to diols, some of which were esterified to the newly formed acids, and some possibly transesterified with glyceride. Triglyceride appeared to be only partially intact and may be partially transesterified with the new acids and diols. In contrast, the control reaction showed only the unreacted starting material.

EXAMPLE 12

Bioconversion of 2-hexyldecanol (Eutano G-16)

The bioconversion of 2-hexyldecanol (Eutanol G-16) was tested following the procedures set forth in Example 3. Recovery was 0.34 g or 70%. NMR analysis showed the starting hydroxyl remained unoxidized. The terminal CH3 were depleted approximately 15%, forming primary OH or acid. Products found were carboxy-2-hexyldecanol and hydroxylated 2-hexyldecanol. NMR analysis of the control sample showed only peaks expected for the product, with a few minor components, including a vinylidene olefin and an α-branched aldehyde, both still present in the oxidized product. Analysis of the control revealed no oxidation of the terminal methyl group.

EXAMPLE 13

Bioconversion of Hexadecyl Acetate

The bioconversion of hexadecyl acetate was tested following the procedures set forth in Example 3. Recovery was 0.24 g or 28%. NMR analysis showed that the acetate was completely gone, either lost in extraction or utilized by the organism as an energy source. The resulting primary OH was 85% gone, and the terminal $CH_3$ was 95% gone, oxidized to 1,16-hexadecanedioic acid. The rate of oxidation appeared higher than for simple alcohols, such as the dodecanol and oleyl alcohol, with hexadecamediac acid as the product. Interestingly, again some unsaturation was present. No triglyceride was seen.

EXAMPLE 14

Bioconversion of Hexadecyl Pelargonate

The bioconversion of hexadecyl pelargonate was tested following the procedures set forth in Example 3. Recovery was 0.24 g (48%). The NMR results showed the terminal $CH_3$ was reduced about 50%, and the expected 1,16-hexadecanedioic acid was formed. Also, some ester of primary OH, about 25% of the starting ester linkages, and some free primary OH were observed. Significant hydrolysis and oxidation had occurred.

EXAMPLE 15

Bioconversion of Sclareol

The bioconversion of sclareol was tested following the procedures set forth in Example 3. Recovery was 0.39-g (78%). Proton and C13 APT NMR analysis showed no differences from the starting material. (The sclareol was not pure, showing an unidentified impurity, estimated at about 10%.)

EXAMPLE 16

Bioconversion of Polyethylene Glycol

The bioconversion of polyethylene glycol was tested following the procedures set forth in Example 3. This sample was water-soluble and thus not ether extractable. Therefore, the total sample was acidified with HCl, diluted 5:1 in acetone, and the precipitated salts filtered out. The liquid was allowed to evaporate in a hood at room temperature. The residue was then rinsed with acetone-d6 for NMR analysis. Surprisingly this showed some oleic acid, some polypropylene glycol from the SAG-471, and polyethylene glycol. There was no evidence of any PEG ester or terminal acid. Thus any PEG oxidized was not recoverable with the acetone.

EXAMPLE 17

Bioconversion of Trans-2-nonene

The bioconversion of trans-2-nonene was tested following the procedures set forth in Example 3. Recovery was very low. NMR analysis showed some evidence of a non-2-enoic acid, possibly non-2-enedioic acid, but also triglyceride, internal chain unsaturation, and some much longer chain length material that might be a simple fatty triglyceride.

EXAMPLE 18

Bioconversion of 7-trans-tetradecene

The bioconversion of 7-trans-tetradecene was tested following the procedures set forth in Example 3. NMR analysis showed that only 3.5% of the starting terminal $CH_3$ remained. Most was converted to 7-trans-tetradecenedioic acid and 14-hydroxytetradeceneoic acid, with a small amount of free primary hydroxyl and approximately 0.2-0.3% esterified primary hydroxyl. Interestingly, about 20-25% of the sample contained fatty type cis unsaturation. NMR analysis of the starting olefin showed a similar cis/trans isomer mix.

EXAMPLE 19

Bioconversion of 2-ethylhexanoic Acid

The bioconversion of 2-ethylhexanoic acid was tested following the procedures set forth in Example 3. A very small sample was recovered The $CH_3$:$CH_2COOH$ ratio appeared to be about 1:1. Unsaturation was also present, and the $CH_2$ chain length was closer to oleic acid than to the shorter starting material or to the desired oxidation products. Thus, this material appears to have been nearly totally consumed or lost in extraction.

EXAMPLE 20

Bioconversion of 6-dodecyne

The bioconversion of 6-dodecyne was tested following the procedures set forth in Example 3. Another very low recovery sample (possibly because of volatility during reaction). NMR analysis showed some normal fatty olefinic unsaturation. Some triglyceride and terminal $CH_3$ amounts were rather high, indicating the recovered sample was high in normal fat, and very low in reaction product. Some residual alkyne and some ester of primary hydroxyl was present.

EXAMPLE 21

Bioconversion of Ocenol Oleyl Alcohol

The bioconversion of ocenol oleyl alcohol was tested following the procedures set forth in Example 3. NMR analysis showed that the terminal $CH_3$ was 80% gone, apparently replaced by 1,18-octadecenedioic acid and 18-hydroxyoctadeceneoic acid. In addition, primary OH was significantly reduced, with only 13% remaining as free OH and 4% present as an ester, as well as esters of oleyl alcohol. Thus the sample appears to be high in octadecanedioic acid, but with some 18-hydroxyoleic acid and its esters, as well as esters of oleyl alcohol. This sample was the first to show a little triglyceride (about 1%).

EXAMPLE 22

Bioconversion of Generol 122N Sterol Mix

The bioconversion of a Generol 122N sterol mix was tested following the procedures set forth in Example 3. NMR analysis showed only unreacted starting materials.

EXAMPLE 23

Toxicity Tests of Additional Substrates

Additional substrates were to be tested for bioconversion following a slightly different protocol than the one noted above in Example 3. Those substrates also had to be tested for toxicity similar to the test described in Example 2, to determine the highest concentration at which a substrate could be added to a culture broth without being toxic, inhibiting growth, or interfering with the bioconversion process. *C. tropicalis* was grown in the presence of the substrate at three different concentrations and growth was monitored spectrophotometrically. In contrast to Example 2, all test substrates were added directly to the culture medium without dissolving in solvent. The tests were completed as follows:

On the first day, H5343 was grown in YPD medium (25.0 ml seed culture) overnight on a rotary shaker at 30° C. and 250 rpm. The next day 1.0 ml of the seed culture was used to inoculate a new flask of 50 ml YPD. This culture was grown overnight on a rotary shaker at 30° C. and 250 rpm. 25 ml of the YPD broth was added to each of three 250 ml baffled shake flasks to which either 1%, 0.5% or 0.1% (either w/v or v/v, depending upon the state of the test substrate) of the test substrate had been added.

Two control flasks were each inoculated with H5343 in 25 ml YPD. All flasks were incubated on a rotary shaker at 30° C. and 250 rpm.

After 24 hours incubation, the absorbance at 600 nm of the test and control flask cultures was determined, using uninoculated YPD broth as blank. Cultures were diluted so that the $OD^{600\ nm}$ measured between 0.15 and 0.3.

Table 4 shows that many of the substrates to be tested were not toxic at a concentration of 1% or less. Other substrates were found to inhibit growth at high concentration, but not at lower concentrations, while some inhibited fairly strongly even at the lowest concentration. For strongly inhibitory substrates, a concentration of 0.1-0.2% was chosen for the bioconversion tests. The concentration used in the bioconversion tests is shown in Table 4.

TABLE 4

Spectrophotometric Data of Toxicity Tests of Substrates on *C. tropicalis*

| Substrate | Absorbance at 600 nm | | | Concentration in Bioconversion Test |
|---|---|---|---|---|
| Concentration [%] | 1.0% | 0.5% | 0.1% | |
| Control | 34 | 34 | 34 | |
| Dodecylvinylether | 7.33 | 12.63 | 20.43 | 0.5% |
| 1,2-Epoxytetradecane | 29.83 | 10.63 | 14.83 | 1.1% |
| 1-Octadecene | 34.7 | 36.33 | 34.93 | 1.0% |
| 1-Hexadecene | 37.93 | 35.33 | 38.99 | 1.0% |

TABLE 4-continued

Spectrophotometric Data of Toxicity Tests of Substrates on *C. tropicalis*

| 2-Hexydecanoic acid | 41.53 | 35.33 | 27.73 | 1.0% |
|---|---|---|---|---|
| Butylsulfone | 1.503 | 2.723 | 22.033 | 0.5% |
| 3-Octanone | 1.229 | 0.909 | 31.33 | 0.27% |
| Propylcyclohexane | 1.201 | 34.12 | 44.13 | 0.5% |
| Hexyl Ether | 3.33 | 13.21 | 12.85 | 0.5% |
| Pentyl Ether | 1.813 | 1.863 | 2.033 | 0.25% |
| Butylcyclohexane | 20.33 | 21.13 | 22.03 | 1.0% |
| 2-Butyl-1-octanol | 6.213 | 8.973 | 10.53 | 0.5% |
| Butylsulfone | 12.25 | 14.21 | 5.61 | 0.25% |
| Butylmalonic Acid | 8.53 | 27.13 | 27.43 | 0.5% |
| 2-Butyloctanoic acid | 4.41 | 4.63 | 5.87 | 0.29% |
| Butylsulfoxide | 5.81 | 11.37 | 15.63 | 0.5% |
| 3-Hexylthiophene | 1.223 | 1.033 | 0.933 | 0.24% |
| 2-Hexyl-1-decanol | 11.93 | 19.73 | 24.43 | 0.5% |
| 1,2-Hexadecanediol | 2.013 | 3.033 | 3.103 | 0.5% |
| VMLP Naphtha | 2.95 | 3.8 | 14.4 | 0.25%, 0.5% |
| Diisobutylene | 7.0 | 5.05 | 23.0 | 0.25%, 0.5% |
| 2-Octanol | 0.285 | 0.235 | 0.250 | Not Tested |

| Substrate Concentration [%] | 0.6% | 0.3% | 0.06% | |
|---|---|---|---|---|
| 3-Butyl-(ethylpentyl)oxazolidine | 1.18 | 0.245 | 12.5 | 0.1% |
| 2-Methyl-3-heptanone | 0.125 | 0.099 | 19.2 | 0.1% |
| Ethylcyclohexane | 16.5 | 2.03 | 9.45 | 0.2% |
| Methylcyclohexane | 0.16 | 15.6 | 13.7 | 0.3% |

EXAMPLE 24

Bioconversion Testing of Additional Substrates (Phase II)

Using the data generated in Example 23, the bioconversion testing was performed using substrate concentrations determined to be neither lethal nor inhibitory in concentrations noted above in Table 4. The test substrate was added directly to a shake flask, either as a solid or as a liquid. A revised shake flask protocol was utilized for the evaluation of yeast strains for diacid production activity.

A single isolated colony was inoculated into 50 ml YPD broth in a 500 ml baffled shake flask. The mixture was then incubated 24 hours at 30° C. and 300 rpm on a rotary shaker-incubator.

15 ml of the YPD-grown culture was then transferred into 135 ml DCA2 medium in a 1000 ml baffled shake flask for a total volume of 150 ml. (The DCA2 medium was prepared by combining 3 g BACTO® Peptone, 6 g yeast extract, 3 g sodium acetate, 7.2 g $K_2HPO_4$, and 9.3 g $KH_2PO_4$ with Milli-Q® Water to produce 1L. Then, 117 ml of the DCA2 mix was added to 15 ml 50% (w/v) glycerol in a 1000 ml baffle flask and autoclaved. The mixture was then allowed to cool and added to 3 ml 50×YNB (334 g/L).) 100 µl of sterile 1:10 SAG 471 antifoam solution was added to each flask. The mixture was then incubated for 24 hours at 30° C. and 300 rpm on a rotary shaker-incubator.

Cells from the DCA2-grown culture were then harvested by centrifugation at 5000 rpm for 5 minutes. The spent broth was poured off and each cell pellet resuspended in 150 ml DCA3 without glycerol (approximately 1.1 times concentration of DCA2 culture). (The DCA3 was prepared by adding 975 ml 0.3 M $KHPO_4$ buffer, pH 7.5 (0.3 M $K_2HPO_4$ solution adjusted to pH 7.5 with 0.3 M $KH_2PO_4$ solution), to 25 ml YNB. The mixture was increased to 1 L with Milli-Q® water, mixed, and filter sterilized.) A 50 ml aliquot of this DCA3 suspension was added to a 500 ml baffled shake flask containing appropriate amount of substrate, as determined by toxicity analysis. 100 µl of a 1:10 dilution of SAG 471 antifoam was added to each flask. The flask was then incubated at 30° C. and 300 rpm on a rotary shaker-incubator.

One hour after initial induction, 2 ml of a sterile 50% (w/v) glycerol solution was added to each flask. Eight hours after induction, an additional 1 ml of the glycerol solution was added to each flask. The reaction was stopped after 24-30 hours in all flasks by placing the flasks in a −20° C. freezer.

For the extraction of the product, the frozen shake flask sample was first thawed in a 37° C. water bath. 5 ml 12N HCl was added to the sample flask and well mixed. The acidified sample was poured into a 250 ml separatory funnel. 60 ml ethyl ether and 40 ml petroleum ether were combined into the empty sample shake flask and swirled well to mix and rinse flask. This was added to the separatory finnel, which was capped and shaken for 1 minute, pausing occasionally to release gas pressure. After standing for 5 minutes, the water layer was removed by decanting into the empty shake flask. The upper solvent layer was decanted into 50 ml centrifuge tubes and centrifuged for 15 minutes in a tabletop centrifuge at 3500 rpm. The ether layer was transferred by pipette to a collection beaker for evaporation.

This extraction procedure was repeated on the aqueous layer with the exception that 30 ml ethyl ether and 20 ml petroleum ether were added to the aqueous layer prior to extraction. The two ether extracts were combined in the beaker and the solvents were allowed to dry at ambient temperatures, leaving product behind. The product was redissolved in a small amount of ethyl ether and was transferred to a tared HPLC vial and the solvent was allowed to evaporate. The sample weight was taken by calculating the difference between the weigh of the sample+HPLC vial and the tared weight of the vial itself. The percent recovery was determined by dividing the weight of the recovered sample by the weight of the sample originally added to the flask and multiplying the result by 100.

The sample was then submitted first for NMR analysis and, if evidence of oxidation was observed, was later submitted for GC/MS analysis.

EXAMPLE 25

Bioconversion of Butylcyclohexane

The bioconversion of butylcyclohexane was tested following the procedures set forth in Example 24. Recovery was low; 0.05 g was recovered from 0.537 g starting material (9.3% recovery). This low recovery reflects the volatility of the test substrate. The NMR results obtained for this sample indicate that of the sample recovered, a small but significant portion was determined to be the polypropylene glycol from the SAG 471 antifoam. It was found to contain considerable carboxylic acid. Some portion of that carboxylic acid was thought to be the anticipated product. The sample was found to contain material that was far more linear than expected, and demonstrated chain unsaturation and polyunsaturation. It also showed a little triglyceride. Finally, the sample demonstrated an oxygen bearing CH, indicating oxidation of the chain off the ring, to cyclohexyl ester or ether. The products noted were 2-butylcyclohexanone, 4-cyclohexylbutanol, 4-(2-hydroxycyclohexyl)butanol, 4-(2-hydroxycyclohexyl) butanoic acid, cyclohexylbutanoic acid, and 4-cyclohexyl-2-hydroxybutanoic acid.

The GC/MS results indicated that the expected reaction product, cyclohexylbutyrate, as well as the intermediate alcohol, was formed. Surprisingly, oxidations of the cyclohexane ring were also found. Additionally, some oxidation of the alpha carbon on the butyl group was observed as well. Since recovery was low, the individual reaction products represented only small quantities, but indicated additional oxidation capabilities for this organism besides ω-oxidation. As these results were obtained in shake flask experiments, the product type and quantity might be influenced by a controlled substrate feed in a fermenter vessel.

EXAMPLE 26

Bioconversion of Propylcyclohexane

The bioconversion of propylcyclohexane was tested following the procedures set forth in Example 24. Recovery was only 0.049 g from 0.252 g starting material (19.4% recovery). This low recovery reflects the volatility of the test substrate. The NMR results obtained for this sample indicate that of the sample recovered, a small but significant portion was determined to be the polypropylene glycol from the SAG 471 antifoam. The sample, however, was found to contain considerable carboxylic acid, with a portion of that carboxylic acid was thought to be the anticipated product. The sample was found to contain material that was far more linear than expected, and contained chain unsaturation and polyunsaturation. The methyl to acid ratio indicates considerable di-acid in the sample. As with the butylcyclohexane reaction, an oxygen bearing CH, indicating oxidation of the chain off the ring to cyclohexyl ester or ether, was observed. The products found were 3-(2-hydroxycyclohexyl)propanoic acid, cyclohexylpropanoic acid and 3-cyclohexyl-2-hydroxypropanoic acid.

The GC/MS results were similar to what was observed with butylcyclohexyane in that the expected product, cyclohexyl-propionic acid (the main product), was detected. Oxidation of the cyclohexane ring was also found in small amounts. Additionally, some oxidation of the alpha carbon on the propyl group was observed as well.

EXAMPLE 27

Bioconversion of Ethylcyclohexane

The bioconversion of ethylcyclohexane was tested following the procedures set forth in Example 24. Recovery was 0.052 g from 0.100 g starting material (52% recovery). The NMR results obtained for this sample indicate the presence of a little BHT and polypropylene glycol, plus the same unknown aromatic. It is a predominantly linear carboxylic acid, higher in di-acid than the methylcyclohexane product. Also present was some triglyceride, a 1,3-diglyceride, and the same sterol as above, though at a lower level. No starting material remained. However, a little cyclohexylacetic acid has also apparently been made, but far less than the fatty derived material.

The results of the GC/MS analysis were in agreement with the NMR data in detecting the expected product, cyclohexylacetate, in small amounts. In this case, however, neither oxidations of the cyclohexane ring nor of the alpha carbon of the acetyl group were detected.

EXAMPLE 28

Bioconversion of Methylcyclohexane

The bioconversion of methylcyclohexane was tested following the procedures set forth in Example 24. Recovery was 0.055 g from 0.150 g starting material (36.7% recovery). The NMR results obtained for this sample indicate that the vast majority of the small sample recovered was a fatty triglyceride with some 1,3-diglyceride and some carboxylic acid. Also seen was some highly branched material, possibly some type of sterol like ergosterol (though not with a double bond at position 5). A little polypropylene glycol (antifoam), BHT (from extraction solvent), and some unidentified aromatic were also found. No methylcyclohexane was seen. Any product was minor, if present at all. Because of these results, this sample was not submitted for GC/MS.

EXAMPLE 29

Bioconversion of Naringenin
(4',5,7-trihydroxyflavanone)

The bioconversion of naringenin (4',5,7-trihydroxyflavanone) was tested following the procedures set forth in Example 24. Naringenin was selected for testing to determine if *C. tropicalis* was capable of oxidizing it to the corresponding isoflavone. Recovery was 0.222 g from 0.503 g starting material (44.1% recovery). Because of solubility problems, the NMR for this sample was examined in acetone-d6 instead of $CDCl_3$. The recovered sample was nearly identical to the starting material. The only loss was that of a minor ethyl acetate contaminant in the starting material, probably a crystallization solvent. New peaks were only a minor amount of residual ethyl ether, trace SAG 471 antifoam, and a small amount of unsaturated fatty acid, possibly partly oxidized to diacid. This is probably a fatty acid made by the organism. No new aromatic components were seen. Low recovery was probably due to poor extraction due to partial solubility in water, though it is possible the material may have been metabolized. The conclusion from this test is that naringenin is not oxidized by *C. tropicalis*.

The GC/MS results confirmed the NMR analysis, indicating nothing but starting material in the extracted sample.

EXAMPLE 30

Bioconversion of 2-Hexyl-1-decanol (Guerbet Alcohol)

The bioconversion of 2-hexyl-1-decanol (Guerbet alcohol) was tested following the procedures set forth in Example 24. This substrate was selected to determine how easily the terminal methyl of the hexyl moiety is oxidized. It is also another example of a Guerbet alcohol and offers another test of the capability of *C. tropicalis* to oxidize a primary alcohol attached to a one-carbon chain on a branched compound. Recovery was good, 0.244 g from 0.255 g starting material (95.7% recovery). The NMR results obtained for this sample indicate that none of the starting alcohol functionality had oxidized to acid (or ester). However, about 16% of the alcohol had esterified. Significant carboxylic acid functionality was seen. Approximately 9% of original terminal $CH_3$ had oxidized to alcohol, of which 18% was esterified. About 55-60% of terminal $CH_3$ had oxidized to acids, part of which were esterified. Residual $CH_3$ was still significant. Interestingly, there was a little unsaturation.

The GC/MS profile demonstrated that both the C-8 and the C-6 side chain methyl groups were oxidized to the alcohol and then the acid, as expected. Products found were 2-(6-hydroxyhexyl)-1-docanol, 2-hexyl-1,10-decanediol, 7-hydroxymethyl-pentadecanoic acid, 10-hydroxy-9-n-hexyl-decanoic acid, 15-hydroxy-7-hydroxymethyl-pentadecanoic acid, 15-hydroxy-9-hydroxymethyl-pentadecanoic acid, and 7-hydroxymethyl-1,15-pentadecanedioic acid. There was no evidence of any oxidation of the initial primary alcohol, however.

EXAMPLE 31

Bioconversion of 2-Hexyldecanoic Acid

The bioconversion of 2-hexyldecanoic acid was tested following the procedures set forth in Example 24. This substrate was chosen to determine if a triacid product could be made from the branched acid starting material. Recovery was 0.469 g from 0.528 g starting material (88.8% recovery). The NMR results obtained for this sample indicate that slightly over half the starting terminal $CH_3$ groups remained, while less than half were oxidized to acid or hydroxyl. Some was esterified to branched acid, and some to linear. It was not certain if there was any tri-acid, or only mono and di-acids. Again, some chain unsaturation was seen. The products found were 2-(6-hydroxyhexyl)-1-decanoic acid, 10-hydroxy-2-(6-hydroxyhexyl)-decanoic acid, 7-carboxy-pentadecanoic acid, 9-carboxy-pentadecanoic acid, 15-hydroxy-7-carboxy-pentadecanoic acid, and 15-hydroxy-9-carboxy-pentadecanoic acid.

The GC/MS profile showed that both the C-8 and the C-6 side chain methyl groups were oxidized to the alcohol and at least one side chain was oxidized to acid. Unfortunately there was no evidence of any formation of the triacid. In principle, since the analogous Guerbet alcohol described previously showed oxidation of both terminal methyl groups to the acid, this material should also oxidize both.

EXAMPLE 32

Bioconversion of 1-Hexadecene

The bioconversion of 1-hexadecene was tested following the procedures set forth in Example 24. A longer-chain α-olefin than was previously tested was chosen to confirm that the (ω,ω-1)-dihydroxy fatty acid could be produced. Recovery was 0.358 g, from 0.502 g starting material (71.3% recovery). The diols made may have been slightly water soluble and partially lost in extraction. The NMR results obtained for this sample indicate that about 70% of terminal $CH_3$ was oxidized to 15,16-dihydroxyhexadecanoic acid. About 50% of vinyl unsaturation remained, 50% oxidized to diol. IR indicated the presence of some ester. Again, some chain unsaturation was seen, indicating the organism may be making fatty acids.

The GC/MS data confirmed the results of the NMR. The (ω,ω-1)-dihydroxy fatty acid was formed as the major product in the reaction.

EXAMPLE 33

Bioconversion of 2-Butyl-1-octanol

The bioconversion of 2-butyl-1-octanol was tested following the procedures set forth in Example 24. This Guerbet alcohol was selected to determine if the terminal methyl of the butyl group could be oxidized to the acid. Recovery was 0.201 g from 0.254 g starting material (79.1% recovery). IR examination showed some carboxylic acid, and residual OH, plus a little ester. NMR indicated about half the $CH_3$ groups had oxidized, mostly to acid, but a little to terminal OH. The alpha branched OH appears to be un-oxidized, but about 10-15% of these starting OH groups were esterified. Again, a significant amount of unsaturated fatty material was seen. The products found were 2-(6-hydroxybutyl)-1-docanol, 2-propyl-1,8-octanediol, 7-hydroxymethyl-undecanoic acid, 8-hydroxy-7-n-propyl-octanoic acid, 11-hydroxy-5-hydroxymethyl-undecanoic acid, 11-hydroxy-7-hydroxymethyl-undecanoic acid, and 7-hydroxymethyl-1,11-undecanedioic acid.

The GC/MS profile showed that both the C-4 and the C-6 side chain methyl groups were oxidized to the alcohol and then the acid, as expected. As with 2-hexyl-1-decanol, there was no evidence of any oxidation of the initial primary alcohol.

EXAMPLE 34

Bioconversion of Dihexyl Ether

The bioconversion of hexyl ether was tested following the procedures set forth in Example 24. This substrate was chosen for testing to determine if the R-group attached to the aliphatic chain could be an ether. Recovery was 1.049 g from 0.261 g starting material (402% recovery). The sample was diluted in acetone-d6 for NMR examination. As with other samples, there was a little unsaturated fatty acid, some polypropylene glycol (SAG 471), and a minor amount of triglyceride. Of primary concern, however, was the ether bond remaining intact, and about 80% of the $CH_3$ oxidizing to carboxylic acid.

The GC/MS data confirmed that the expected diacid, 7-oxa-1,13-tridecanedioic acid, was the major product.

EXAMPLE 35

Bioconversion of Dodecylvinyl Ether

The bioconversion of dodecylvinyl ether was tested following the procedures set forth in Example 24. This substrate was selected for testing to determine the fate of the terminal diol attached directly to the ether functionality. It was also of interest to determine if the terminal methyl group could be oxidized. Recovery was 0.233 g from 0.260 g starting material (89.6% recovery). The NMR results obtained for this sample indicate that the vinyl group was missing. Also, about 60% of the terminal $CH_3$ had oxidized to dodecanedioic acid, with a small amount of primary OH. However, the peaks demonstrating carboxylate were stronger than expected, indicating $C_{12}$ diacid formation. Other major functionalities noted included an alkyl alkoxy glycolate (ether-ester), and surprisingly, an acetaldehyde di-alkyl acetal.

The GC/MS profile demonstrated that although there appears to be a tiny amount of the expected ($\omega,\omega$-1)-dihydroxy fatty acid the major product was the $C_{12}$ diacid. It appears that the terminal diol was cleaved and the ether group was oxidized to the acid, with the alcohol intermediate detected as well.

EXAMPLE 36

Bioconversion of Dibutyl sulfone

The bioconversion of dibutyl sulfone was tested following the procedures set forth in Example 24. Recovery was 0.209 g from 0.26 g starting material (80.4% recovery). NMR showed a little SAG 471, a little unsaturated fatty acid, and minor unidentified material, but predominantly unreacted dibutyl sulfone. No GC/MS analysis was performed.

EXAMPLE 37

Bioconversion of Butylmalonic Acid

The bioconversion of butylmalonic acid was tested following the procedures set forth in Example 24. Recovery was 0.325 g from 0.253 g starting material (128% recovery). This sample was dissolved in acetone-d6 for NMR analysis, which indicated considerable unreacted starting material remained, with some normal unsaturated fatty acid, a little SAG 471, and little or no desired tri-acid. No GC/MS analysis was performed.

EXAMPLE 38

Bioconversion of Butyl Sulfoxide

The bioconversion of Butyl sulfoxide was tested following the procedures set forth in Example 24. Recovery was 0.152 g from 0.259 g starting material (58.7% recovery). The NMR results obtained for this sample indicate that a small amount of unsaturated fatty acid was present, along with some SAG 471. The main components however were approximately 80% dibutylsulfoxide and approximately 20% dibutyl sulfone. No GC/MS analysis was performed.

EXAMPLE 39

Bioconversion of 2-Butyloctanoic Acid

The bioconversion of 2-butyloctanoic acid was tested following the procedures set forth in Example 24. Recovery was 0.114 g from 0.144 g starting material (79.2% recovery). NMR showed predominantly unreacted starting material, with a little polypropylene glycol (antifoam), BHT, and minor ether peroxides and other by-products. Based on data from the corresponding Guerbet alcohol, one would have expected this material to be oxidized to some degree.

EXAMPLE 40

Bioconversion of 3-Hexylthiophene

The bioconversion of 3-hexylthiophene was tested following the procedures set forth in Example 24. Recovery was 0.109 g from 0.122 g starting material (89.3% recovery). NMR indicated the material was mostly unreacted starting material. Several minor peaks were seen, which remain unidentified, but did not indicate the expected oxidation of the terminal $CH_3$ to acid. Instead, it appears some polyhydric material was formed, possibly from the solubilization of a sugar adduct to an organically soluble material. A small amount of polypropylene glycol and minor unsaturatedlfatty acid or ester was also seen. No GC/MS analysis was performed.

EXAMPLE 41

Bioconversion of 1-Octadecene

The bioconversion of 1-octadecene was tested following the procedures set forth in Example 24. Recovery was 0.287 g from 0.502 g starting material (57.2% recovery). The NMR results obtained for this sample indicate that some fatty acid was present, and some residual $\alpha$-olefin, but about half the olefin had oxidized to 1,2-diol, and about 80% of the terminal $CH_3$ had oxidized to acid, indicating that the expected ($\omega,\omega$-1)-dihydroxy fatty acid, 17,18-dihydroxyoctadecanoic acid was formed. No GC/MS analysis was performed.

EXAMPLE 42

Bioconversion of Dipentyl Ether

The bioconversion of pentyl ether was tested following the procedures set forth in Example 24. Like the hexyl ether, this substrate was tested to determine if the terminal methyl groups of the pentyl chains could be oxidized. Recovery was 0.100 g from 0.123 g starting material (81.3% recovery). NMR results indicate the ether remained intact, and about 50% of the terminal $CH_3$ was oxidized to 6-oxa-1,11-undecanedioic acid. Some intermediate primary OH and an ester of primary OH was also seen. This result confirmed that the terminal methyl on the $C_5$ chain could be oxidized to the acid. No GC/MS analysis was performed.

EXAMPLE 43

Bioconversion of 3-Octanone

The bioconversion of 3-octanone was tested following the procedures set forth in Example 24. This substrate was tested to determine if C. tropicalis could oxidize the terminal methyl group (either the $C_4$ or $C_2$) attached to a ketone functionality. Recovery was 0.069 g from 0.135 g starting material (51% recovery). NMR showed some of the product to be fatty acid. Some PPG and some BHT (ether stabilizer) was also seen. Interestingly, the 3-octanone was nearly completely gone, with 3-octanol being seen. Product loss was likely due to volatility during solvent evaporation after extraction. No GC/MS analysis was performed.

EXAMPLE 44

Bioconversion of 1,2-Epoxytetradecane

The bioconversion of 1,2-epoxytetradecane was tested following the procedures set forth in Example 24. This substrate was selected to confirm the results of the tests on Epoxy Soya, where it was found that the epoxy rings were split to form a diol. Recovery was 0.349 g from 0.534 g starting material (65.4% recovery). The NMR results obtained for this sample indicate that epoxy was completely gone, replaced by diol. Most of the terminal $CH_3$ (about 80%) was oxidized to the acid 13,14-dihydroxytetradecanoic acid. Since the NMR results were fairly convincing, no GC/MS analysis was performed.

EXAMPLE 45

Bioconversion of 1,2-hexadecanediol

The bioconversion of 1,2-hexadecanediol was tested following the procedures set forth in Example 24. This substrate was tested to demonstrate the ability to form a ($\omega,\omega$-1)-dihydroxy fatty acid. Recovery was 0.138 g from 0.253 g starting material (54.5% recovery). NMR shows the 1,2-diol to be unchanged, as expected from olefin studies. But, interestingly, $CH_3$ oxidation to the 15,16-dihydroxyhexadecanoic acid was lower than seen with octadecene, because the starting material was solid. Conversion was only about 30%. Some fatty unsaturation and minor polypropylene glycol were also seen. Since the NMR results were fairly convincing, no GC/MS analysis was performed.

EXAMPLE 46

Bioconversion of Di-isobutylene

The bioconversion of di-isobutylene was tested following the procedures set forth in Example 24. This substrate was tested because it is a potential solvent for use in the C18:1 diacid recovery process. It was important to determine the fate of any residual DIB that might be left in recovery side streams that could potentially be recycled back to later fermentations. Recovery was 0.029 g from 0.125 g starting material (23.2% recovery). The NMR results showed long chain linear unsaturated mono and di-acids, about 15% of which were present as triglycerides. Also seen was a little polypropylene glycol (from the SAG 471 antifoam) along with some trace BHT, possibly a stabilizer in the extraction solvent. There was little evidence of any branched materials, indicating the test substrate was either degraded or was lost during testing or extraction. It also indicated that no non-volatile oxidation products were formed in the process. Because of this result, no GC/MS analysis was performed.

EXAMPLE 47

Bioconversion of VMLP Naptha

The bioconversion of VMLP naptha was tested following the procedures set forth in Example 24. Recovery was 0.024 g from 0.125 g starting material (19.2% recovery). The NMR results obtained for this sample indicate that little or no VMLP oxidation product appeared to have been formed. The product was predominantly a mix of linear unsaturated mono and di-acids, with a small amount of polypropylene glycol. Interestingly, little or no triglyceride was present. Because of this result, no GC/MS analysis was performed.

EXAMPLE 48

Bioconversion of 2-Methyl-3-heptanone

The bioconversion of 2-methyl-3-heptanone was tested following the procedures set forth in Example 24. This was another test for the ability of C. tropicalis to oxidize the terminal methyl group of an aliphatic chain attached to a semi-complex ketone functionality. Recovery was 0.062 g from 0.050 g starting material (124% recovery). The NMR results obtained for this sample indicate the presence of a blend of triglyceride, 1,3-diglyceride, possible ergosterol, BHT, and polypropylene glycol. Some residual starting material was detected. In such a mix, it is difficult to say if desired product has been formed or not. This was not submitted for GC/MS analysis.

EXAMPLE 49

Bioconversion of 3-Butyl-2(1-ethylpentyl)oxazolidine

The bioconversion of 3-butyl-2(1-ethylpentyl)oxazolidine was tested following the procedures set forth in Example 24. Recovery was 0.021 g from 0.100 g starting material (21% recovery). The NMR results obtained for this sample indicate the presence of some apparent fatty derived material, though less than the other samples. BHT, other minor aromatics and polypropylene glycol seen in the other samples were again seen. No residual starting material was seen. Also, the branched carbon between the oxygen and nitrogen of the starting material was totally absent. The low level of the oxidation product in this complex mix made identification difficult. But some significant $CH_3$ was seen, indicating something from the starting material, but ring degradation rather than acid formation. It is also possible that some desired product, may have been made, but being amphoteric, was more soluble in water than in extraction solvent. This sample was not submitted for GC/MS analysis.

EXAMPLE 50

Bioconversion of The Bio-oxidation of 1,4-diethylbenzene

NMR on the sample obtained showed considerable long chain unsaturated fatty material was formed, which was partially oxidized to di-acid. Considerable sterol was also present, plus polypropylene glycol, and a little BHT. Other major aromatic compounds were present, but the starting 1,4-diethyl benzene appeared to be mostly reacted. The predominant product was 4-ethylphenylacetic acid. There appeared to be little or no 1,4-phenylenediacetic acid, the possible di-oxidized product.

A summary of the results of the bioconversion testing described in the above Examples is set forth below in Table 5.

TABLE 5

Summary of screening results

| Chemical Class/R Group | Phase | Chemical Substrate | Reaction or Major Reaction Product |
|---|---|---|---|
| Fatty Acids or Fatty Acid Esters | I | 12-Hydroxystearic acid | 7-hydroxyoctadecanedioic acid |
| | I | Hexadecyl Pelargonate | Terminal methyls oxidized to acids Ester linkage hydrolyzed |
| | I | Castor Oil | Terminal methyls oxidized to acids Considerable transesterification |
| | I | Hexadecyl Acetate | Terminal methyls oxidized to acids Ester linkage hydrolyzed |
| Ethers | II | Dihexyl Ether | α,ω-Diacid |
| | II | Dipentyl Ether | Terminal methyls oxidized to acids |
| | II | Dodecylvinyl Ether | Dodecanedioic acid |
| Alpha Olefins | I | Dodecene | (ω,ω-1) Dihydroxy Fatty Acid |
| | I | Tetradecene | (ω,ω-1) Dihydroxy Fatty Acid |
| | II | Hexadecene | (ω,ω-1) Dihydroxy Fatty Acid |
| | II | Octadecene | (ω,ω-1) Dihydroxy Fatty Acid |
| Alkenes | I | trans-2-nonene | 2-enoic acid (recovery low) |
| | I | 7-trans-tetradecene | 7-trans-tetradecenedioic acid |
| | II | Diisobutylene | No reaction/Volatility |
| Alkynes | I | 6-Dodecyne | No Reaction/Volatility |
| Alcohols | I | 1-Dodecanol | Terminal OH oxidized to acid Some Terminal methyl oxidized |
| | I | Oleyl Alcohol | Octadecenedioic acid |
| | I | 6-Undecanol | No Reaction |
| | II | 2-Octanol | Toxic at 0.1% |
| Branched Alcohols | II | 2-Hexyldecanol | Terminal methyls oxidized to acids |
| | II | 2-Butyl-1-Octanol | Terminal methyls oxidized to acids |
| | II | 1,2-Hexadecanediol | (ω,ω-1) Dihydroxy Fatty Acid |
| Branched Acids | I | 2-Ethylhexanoic Acid | Too Volatile |
| | I | 2-Heptylundecanoic Acid | Terminal methyls oxidized to acids |
| | II | 2-Hexyldecanoic Acid | Terminal methyls oxidized to acids |
| | II | 2-Butyloctanoic Acid | No reaction |
| | II | Butylmalonic Acid | No reaction |
| Ketones | II | 3-Methyl-3-heptanone | No Reaction |
| | II | 3-Octanone | No Reaction |
| Epoxides | I | Epoxy Soya | Terminal methyls oxidized to acids Epoxy groups open to diols |
| | II | 1,2-epoxytetradecane | (ω,ω-1) Dihydroxy Fatty Acid |
| Sulfur Compounds | II | Butylsulfone | No reaction |
| | II | Butylsulfoxide | No reaction |
| | II | 3-Hexylthiophene | Screening in Process |
| Aliphatic Amines | I | Dodecylamine | Toxic at 0.01% |
| Ring Compounds | I | Limonene | No Reaction/Volatility |
| | I | Sclareol | No Reaction |
| | I | Generol | No Reaction |
| | II | Butylcyclohexane | Terminal methyls oxidized to acids |
| | II | Propylcyclohexane | Terminal methyls oxidized to acids |
| | II | Ethylcyclohexane | Terminal methyl oxidized to acid |
| | II | Methylcyclohexane | No Reaction |
| | II | 3-Butyl-2-(1-ethylpentyl) Oxazolidine | No Reaction |
| Miscellaneous | I | PEG | No Reaction |
| | I | PEG200 Monolaurate | Terminal methyls oxidized to acids |
| | I | PEG200 Dilaurate | Terminal methyls oxidized to acids |
| | II | VMLP Naphtha | No reaction |

It will be understood that various modifications may be made to the embodiments disclosed herein and that the above description should not be construed as limiting, but merely as exemplifications of preferred embodiments. Those skilled in the art will envision other modifications within the scope and spirit of the claims appended hereto.

What is claimed is:

1. A process for producing an alcohol comprising culturing Candida sp. in a fermentation medium containing a substrate of the formula $R(CH_2)_nCH_3$ wherein n is $\geq 1$ and R is selected from the group consisting of, ether, saturated primary alcohol, cycloalkyl, aryl, and diol, whereby at least one terminal methyl group of the substrate is oxidized to an alcohol.

2. The process of claim 1 wherein the substrate is dissolved in a solvent prior to contact with the fermentation medium.

3. The process of claim 2 wherein the solvent is an organic solvent.

4. The process of claim 3 wherein the organic solvent is selected from the group consisting of ethanol and hexane.

5. The process of claim 3 wherein the organic solvent is acetone.

6. The process of claim 1 wherein the Candida sp. is selected from the group consisting of C. albicans, C. cloacee, C. guilermondli, C. intermedia, C. lipolytica, C. maltosa, C. parepsilosis, and C. zeylenoides.

7. The process of claim 1 wherein the Candida sp. is C. tropicalis.

8. The process of claim 7 wherein C. tropicalis is substantially β-oxidation pathway blocked.

9. The process of claim 8 wherein *C. tropicalis* is H5343.

10. The process of claim 8 wherein one or more P450 CYP genes, P450 CPR genes, or a combination thereof is amplified in said *C. tropicalis*.

11. The process of claim 1 wherein the substrate is a compound selected from the group consisting of dodecylvinyl ether, dihexyl ether, dipentyl ether, 1-dodecanol, 2-hexyldecanol, 2-butyl-1-octanol, 1,2-hexadecanediol, epoxidized soybean oil, 1,2-epoxytetradecane, butylcyclohexane, propylcyclohexane, ethylcyclohexane, polyethylene glycol 200 monolaurate, polyethylene glycol 200 dilaurate.

12. The process of claim 1 wherein R is an epoxide, alkoxy or diol ester.

\* \* \* \* \*